US00PP08667P

United States Patent [19]

Machin

[11] Patent Number: Plant 8,667

[45] Date of Patent: Mar. 29, 1994

[54] CHRYSANTHEMUM PLANT NAMED SHEENA

[75] Inventor: Barrie J. Machin, Lee-on-Solent, England

[73] Assignee: Goldstock Breeding Limited, Fareham, England

[21] Appl. No.: 965,718

[22] Filed: Oct. 23, 1992

[51] Int. Cl.[5] ..... A01H 5/00

[52] U.S. Cl. ..... Plt./78

[58] Field of Search ..... Plt. 77, 78, 76

*Primary Examiner*—Howard J. Locker

*Attorney, Agent, or Firm*—Foley & Lardner

[57] ABSTRACT

A Chrysanthemum plant named Sheena, particularly characterized by its straight quill-shaped florets carried on strong stems, yellow-white ray floret color with lemon yellow near center, dark leaves; diameter across the face of the capitulum 84–91 mm when fully opened, when grown as a single stem cut mum; flowering response under normal temperatures of 56–60 days after start of short days, plant height of 86–96 cm when grown with 14 long days prior to start of short days, peduncle length of the first lateral at flowering of 8–13 cm and at the fourth lateral of 13–18 cm, and its terminal spray formation.

3 Drawing Sheets

The present invention comprises a new and distinct cultivar of Chrysanthemum, botanically known as *Dendranthema grandiflora,* and referred to by the cultivar name Sheena.

Sheena was originated from a cross made by the inventor, Barrie J. Machin, in a controlled breeding program in Fareham, United Kingdom (U.K.) in 1985. The female parent of Sheena was a seedling known as Super White, described as a cut spray mum, spider type, having white ray florets, diameter of capitulum 89–90 mm when fully open, a flowering response to short days of 69–63 days, a plant height of 91–109 cm when grown with 14 long days prior to start of short days, a peduncle length of the first lateral of 10–15 cm and of the fourth lateral of 17–22 cm, and a terminal spray formation. The above characteristics are based on plants grown in Fareham, U.K.

The male parent of Sheena was a seedling identified as Dark Westland, disclosed in U.S. Plant Pat. No. 4,967 and described as a cut spray mum, spider type, having deep mauve pink ray florets, diameter of capitulum of 75–84 mm, a flowering response of 56 days, a plant height ranging from 86–96 cm when grown with 14 longs days prior to start of short days, a peduncle length of the first lateral of 10–15 cm and of the fourth lateral of 17–22 cm, and a terminal spray formation. The above characteristics are based on plants grown in Fareham, U.K.

Sheena was discovered and selected as one flowering plant within the progeny of the stated cross by Barrie J. Machin March 1985 in a controlled environment in Fareham, U.K.

The first act of asexual reproduction of Sheena was accomplished when vegetative cuttings were taken from the initial selection in January 1987 in a controlled environment in Fareham, U.K. by Barrie J. Machin.

Horticultural examination of controlled flowerings of successive plantings has shown that the unique combination of characteristics as herein disclosed for Sheena are firmly fixed and are retained through successive generations of asexual reproduction.

Sheena has not been observed under all possible environmental conditions. The phenotype may vary with variations in environment such as temperature, light intensity and daylength without, however, any variance in the genotype.

The following observations, measurements and comparisons describe plants grown in Fareham, U.K. under greenhouse conditions which approximate those generally used in commercial greenhouse practice.

The following traits have been repeatedly observed and are determined to be basic characteristics of Sheena which in combination distinguish this chrysanthemum as a new and distinct cultivar:

1. Quill form with all petals rolled their entire length.
2. Generally flat flower comprised essentially of ray florets.
3. Yellow-white ray floret color with lemon yellow toward the center.
4. Diameter across face of capitulum of 84–91 mm when fully opened, when grown as a single stem and spray mum.
5. Flowering response under normal temperatures is 56–60 days after start of short days.
6. Plant height is 86–96 cm when grown with 14 long days prior to short days.
7. Peduncle length of the first lateral at flowering after removing the apical bud without a growth regulator application is 8–13 cm; peduncle length of the fourth lateral at flowering is 15–20 cm.
8. Terminal spray formation.

The accompanying color photographic drawings show typical inflorescence and leaf characteristics of Sheena, with the colors being as nearly true as possible with illustrations of thie type.

Sheet 1 is a color photograph of Sheena grown as a single stem spray cut mum.

Sheet 2 is a black and white photograph of three views of the inflorescence of Sheena.

Sheet 3 is a black and white photograph showing the upper side of the leaves of Sheena at three states of development (mature, intermediate and immature).

Of the commercial cultivars known to the inventor, the most similar in comparison to Sheena is the cultivar identified as Super White. Reference is made to attached Chart A which compares certain characteristics of Sheena to the same characteristics of Super White. The ray floret color of Sheena is distinctly whiter toward the outer part of the capitulum and more lemon toward the center. Sheena has strong straight quill shaped ray florets whereas the ray florets of Super White are open and curved at the ends.

Compared to Yellow Sheena, an induced mutation of Sheena described in pending application Ser. No. 07/966,084 applicant, Sheena has yellow white ray florets with a lemon yellow center. In addition, Yellow Sheena has slightly more upright lateraisl, slightly shorter plant height, and a less widely branching spray form.

In the flowering description color references are made to The Royal Horticultural Society Colour Chart. The color values were determined on plant material grown as a single cut mum in Fareham, U.K. on Aug. 11, 1988.

Classification:

*Botanical.*—*Dendrantema grandiflora* cv. Sheena.

*Commercial.*—Quill spray cut mum.

INFLORESCENCE

A. Capitulum:

*Form.*—Quill with all petals being rolled their entire length.

Type.—Generally flat comprised essentially of ray florets; low profile.

*Diameter across face.*—84–91 mm.

B. Corolla of ray florets:

*Color (general tonality from a distance of three meters).*—White with lemon yellow 4B center.

*Color (upper surface).*—RHS 158D, yellow toward center.

*Color (under surface).*—RHS 158D.

*Shape.*—Quill, straight, carried on strong stems 146B in color.

C. Reproductive organs:

*Androecium.*—There are few disc florets and thus very low pollen.

*Gynoecium.*—Present in all florets. Stigmata develop 3–4 days after pollen production.

PLANT

A. General appearance:

*Height.*—86–96 cm.

*Branching pattern.*—Strong upright growth with relatively long upright laterals form a relatively wide branching spray.

B. Foliage:

*Color (upper surface).*—RHS 137A.

*Color (under surface).*—Lighter than RHS 137A.

*Shape.*—See photograph.

CHART A

COMPARISONS OF PLANTS GROWN AS SINGLE SPRAY STEM CUT MUMS IN FAREHAM, U.K.
Comparison of Sheena and Super white

| Characteristics | Sheena | Super White |
|---|---|---|
| Ray floret color | yellow-white with lemon yellow center | Creamy white |
| Capitulum form | Quill | Spider |
| Diameter across face of capitulum | 89–91 mm | 89–99 mm |
| Spray formation | Compound | Compound |
| Flowering response | 56–60 days | 60–63 days |
| Plant height given 14 long days | 86–96 cm | 91–101 cm |
| Peduncle length: | | |
| First lateral | 8–13 cm | 10–15 cm |
| Fourth lateral | 15–20 cm | 17–22 cm |
| Spray form | Terminal | Terminal |

I claim:

1. A new and distinct Chrysanthemum plant named Sheena, as described and illustrated.

* * * * *

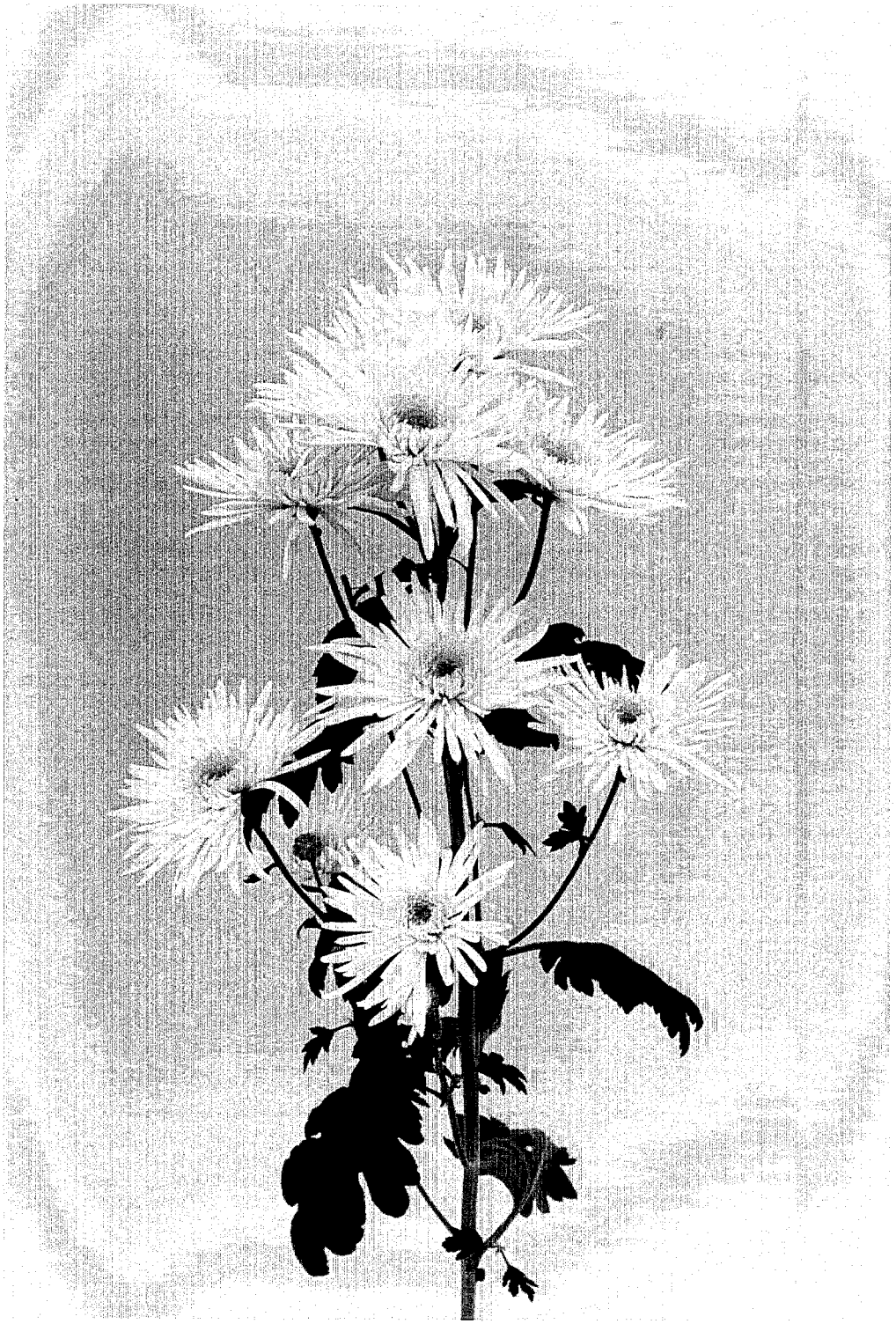

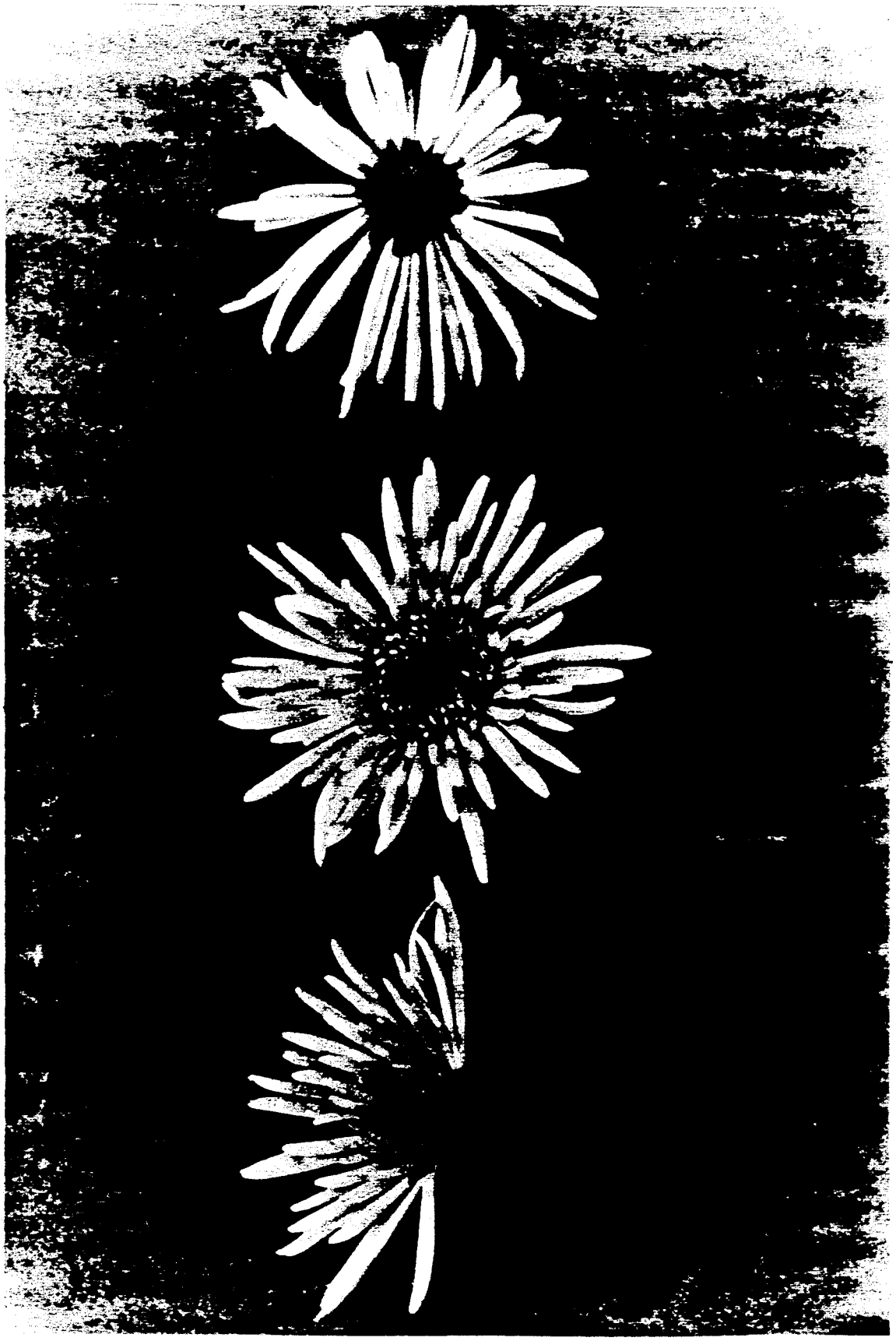

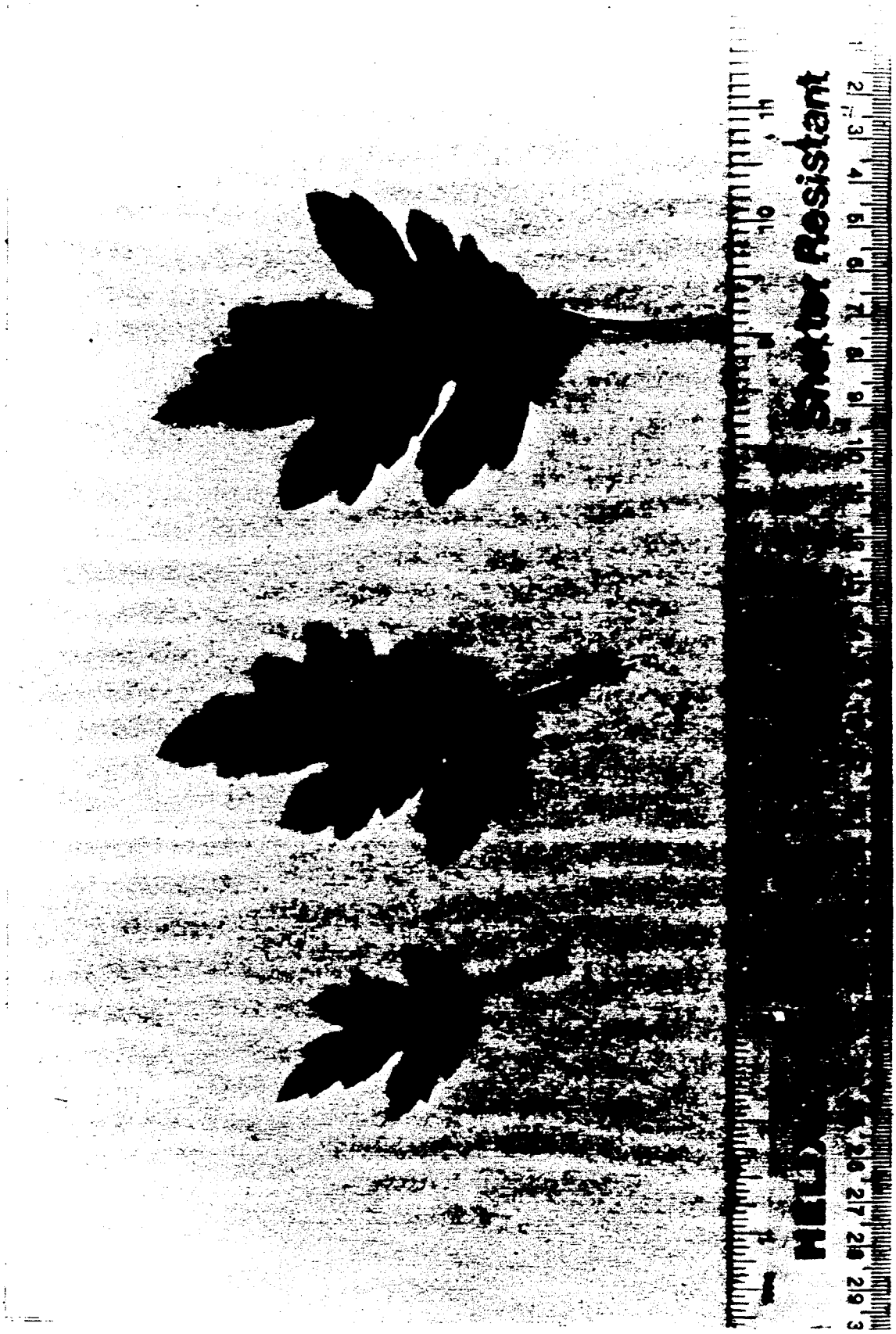
Smut Resistant